United States Patent [19]

Nikles

[11] 3,950,533
[45] Apr. 13, 1976

[54] PYROCATECHOL CARBAMATES AND O-MERCAPTOPHENOL CARBAMATES AND THEIR USE FOR COMBATING PESTS

[75] Inventor: Erwin Nikles, Liestal, Switzerland

[73] Assignee: Ciba-Geigy AG, Basel, Switzerland

[22] Filed: July 22, 1974

[21] Appl. No.: 490,542

Related U.S. Application Data

[60] Division of Ser. No. 162,312, July 13, 1971, Pat. No. 3,843,720, which is a continuation-in-part of Ser. No. 775,584, Nov. 12, 1968, abandoned.

[30] Foreign Application Priority Data

Nov. 10, 1967 Switzerland.................. 15746/67

[52] U.S. Cl. ................................................ 424/300
[51] Int. Cl.² ........................ A01N 9/12; A01N 9/20
[58] Field of Search .................................. 424/300

[56] References Cited
UNITED STATES PATENTS 3,492,335 1/1970 Gubler .............................. 260/479
3,646,220 2/1972 Dachs et al. ...................... 260/609

Primary Examiner—Stanley J. Friedman
Assistant Examiner—Allen J. Robinson
Attorney, Agent, or Firm—Frederick H. Rabin

[57] ABSTRACT

New carbamates, pesticidal preparations containing them as active ingredient and their utility for combating insects, members of the order acarina, nematodes, molluscs and microorganisms are disclosed. The carbamates correspond to the formula

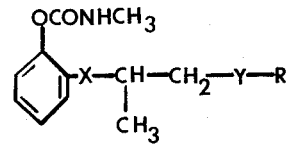

in which X and Y each represents oxygen or sulphur and R represents a lower alkyl, alkenyl or alkynyl group.

2 Claims, No Drawings

PYROCATECHOL CARBAMATES AND O-MERCAPTOPHENOL CARBAMATES AND THEIR USE FOR COMBATING PESTS

CROSS REFERENCE

This is a division of application Ser. No. 162,312, filed on July 13, 1971, now U.S. Pat. No. 3,843,720, which in turn is a continuation-in-part of application Ser. No. 775,584, filed on Nov. 12, 1968, now abandoned.

The present invention provides new carbamates of the general formula:

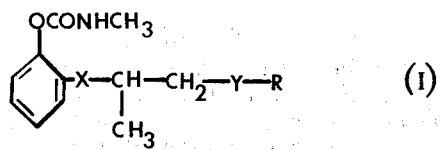

X and Y each represents oxygen or sulphur and R represents a lower alkyl, alkenyl or alkynyl group, pesticidal preparations containing such compounds and methods of combating members of the order Acarina with the new carbamates.

Especially suitable compounds correspond to the formula

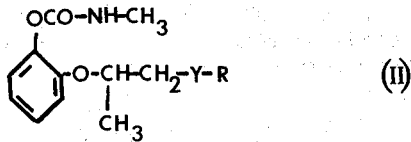

wherein Y and R have the meaning given above.

Due to their outstanding activity those compounds are especially preferred which correspond to the formula

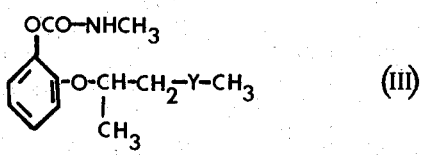

wherein Y has the meaning given above.

As examples of suitable compounds of the formulae I to III there may be mentioned i.a. o-(1-methoxy-2-propoxy)-phenyl-N-methylcarbamate, o-(1-allyloxy-2-propoxy)-phenyl-N-methylcarbamate and o-(1-propargyloxy-2-propoxy)-phenyl-N-methylcarbamate.

The new carbamates can be obtained by methods usually employed for the manufacture of this class of substances, for example, by the reaction of suitable phenols with methylisocyanate, alkyl- or dialkylcarbamic acid chlorides, or by the reaction of suitable phenylcarbonates or phenylchlorocarbonates with methylamine or methylalkylamines.

The new carbamates act as insecticides and acaricides against all stages of development of these pests, and are especially powerful against house flies, aphids, caterpillars, ticks, bugs and beetles, for example, corn beetles and Colorado beetles. Their action is especially powerful against *Phyllodromia germanica, Periplaneta americana, Blatta orientalis, Acheta domestica* and *Rhodnius prolixus.* With regard to contact action, they are greatly superior to the known active substance "carbaryl" (N-methyl-α-naphthyl-carbamate).

When used in larger amounts, the compounds of formula (I) possess a growth-suppressing or growth-retarding action against various representatives of monocotyledon or dicotyledon genera of plants.

When used at a concentration which does not allow any phytotoxic phenomena to arise they also show a good protective action against harmful micro-organisms, for example, against fungi, such as *Alternaria solani, Phytophthora infestans* and *Septoria apii,* as well as against harmful nematodes and their eggs or larvae. Moreover the new compounds can generally be used as microbicides, for example against varieties of Aspergillus, and are also active against molluscs.

The advantage of the carbamates of formula (I) is that they have a pronounced long-term action, which does not allow any impairment to be detected in the dry coating, even after 5 months. After the application, complete protection against, for example, household pests is thus ensured for this period of time. The new carbamates are therefore very suitable for combating pests in the field of hygiene and in storage, also in plant protection.

The compounds according to the present invention can be used by themselves or together with a suitable carrier and/or further additive and/or further pesticidal compounds such as insecticides, acaricides, nematocides, bactericides or fungicides.

By carriers there are above all understood extenders (solvents or solid or liquid diluents). Additives are intended to encompass other substances customary in formulation technology, for example, natural or regenerated mineral substances, suspending agents, emulsifiers, wetting agents, adhesives, thickeners and binders, and also, for example, baits for insects, or fertilisers, if for example an improvement of the soil conditions and growth conditions is desired simultaneously with combating of pests.

Pesticides which contain compounds of formula (I) as active substances can be used in the most various ways and forms, for example in the form of solutions, sprays, dusting powders, scattering agents, granules, spraying powders, emulsions, suspensions, and also so-called fly dishes or fly strips which are impregnated with a solution of the active substances. All compositions may be prepared according to methods well known in the field of pesticide formulation.

As a rule, the agents according to the invention contain 0.005 to about 95% of an active substance of formula I. In individual cases, technically pure active substance can also be employed for combating pests, using an application equipment which provides extremely fine distribution.

The following Examples will illustrate the invention; the parts being by weight.

EXAMPLE 1

1-Methoxy-2-propyl-p-toluenesulphonate

420 Parts of p-toluenesulphonyl chloride are added, in portions, at a temperature of 0°C, to 216 parts of 1-methoxy-2-propanol. Thereafter, 324 parts of pyridine are added drop by drop to the mixture whilst stirring at 0°C, and the mixture is kept for a further 16 hours at this temperature. After dilution with 1000 parts of ice water, the product is extracted with 1000 parts by volume of ether. The ether solution is repeatedly washed with 2 N hydrochloric acid, saturated sodium bicarbonate solution and water, dried over anhydrous sodium sulphate and evaporated. The remaining product is an oil.

O-(1-Methoxy-2-propyloxy)-phenol 90 parts of 44.5% strength sodium hydroxide solution are added drop by drop under nitrogen to a solution of 110 parts of pyrocatechol and 244 parts of 1-methoxy-2-propyl-p-toluenesulphonate in 500 parts by volume of dimethylsulphoxide. During the addition, the temperature rises to 42°C. The mixture is stirred for 14 hours at room temperature, poured into 2000 parts of water, and extracted three times each time with 250 parts by volume of toluene. The toluene solution is washed twice each time with 200 parts of water, and evaporated. The residue is distilled in a high vacuum. Boiling point 70°–82°C/0.04 mm Hg.

O-(1-Methoxy-2-propoxy)-phenyl-N-methyl-carbamate (Compound No. 1)

38 Parts of O-(1-methoxy-2-propoxy)-phenol are dissolved in 250 parts by volume of dry toluene, and mixed with 0.3 parts of triethylene diamine and with 13 parts of methylisocyanate added in portions. The solution is kept for 14 hours at 35°C, and is then evaporated. The product crystallises gradually; melting point 57°C. It can be recrystallised from carbon tetrachloride-cyclohexane.

EXAMPLE 2

O-(1-Methoxy-2-propylthio)-phenol

126 Parts of o-mercaptophenol are added in portions, in a nitrogen atomsphere and whilst cooling, to a stirred mixture of 138 parts of potassium carbonate, 166 parts of potassium iodide and 500 parts by volume of acetone. The mixture is thereafter heated to boiling point and 268 parts of 1-methoxy-2-propyl-p-toluene-sulphonate are added drop by drop. The mixture is boiled under reflux for 24 hours, filtered and evaporated. The residue is taken up in 750 parts by volume of toluene, and washed once with water, and then twice each time with 250 parts by volume of 15% strength sodium hydroxide solution. The alkaline extract is immediately neutralised with hydrochloric acid and extracted with toluene. The toluene solution is dried over anhydrous sodium sulphate, filtered and evaporated. The residue is distilled in a high vacuum.

O-(1-Methoxy-2-propylthio)-phenyl-N-methylcarbamate (Compound No. 2)

45 Parts of o-(1-methoxy-2-propylthio)-phenol are dissolved in 250 parts by volume of dry toluene and mixed with 0.2 parts of diethylene triamine and with 17 parts of methyliocyanate added drop by drop. The solution is kept for 14 hours at 30°–35°C. The oily product is obtained by evaporating the solution in vacuo.

The following compounds are manufactured analogously: (3) o-[1-Ethoxy-2-propoxy]-phenyl-N-methyl-carbamate, (4) o-[1-allyloxy-2-propoxy]-phenyl-N-methylcarbamate, (5) o-[1-propargyloxy-2-propoxy]-phenyl-N-methylcarbamate, (6) o-[1-methylthio-2-propoxy]-phenyl-N-methylcarbamate, (7) o-[1methylthio-2-propylthio]-phenyl-N-methylcarbamate, (8) o-[1-ethoxy-2-propylthio]-phenyl-N-methylcarbamate, (9) o-[1-ethylthio-2-propoxy]-phenyl-N-methylcarbamate, (10) o-[1-ethylthio-2-propylthio]-phenyl-N-methylcarbamate.

EXAMPLES OF FORMULATIONS

Dusting Agents

Equal parts of an active substance according to the invention and precipitated silica are finely ground together. Dusting agents, preferably containing 1–6% of an active substance, can be manufactured therefrom by mixing with kaolin or talc.

Spraying Powders

In order to manufacture a spraying powder, the following components are, for example, mixed and finely ground: 50 parts of active substance according to the present invention, 20 parts of Hisil (highly adsorptive silica), 25 parts of Bolus alba (kaolin), 3.5 parts of a reaction product of p-tert. octylphenol and ethylene oxide and 1.5 parts of sodium 1-benzyl-2-stearylbenzimidazole-6,3'-disulphonate.

Emulsion Concentrate

Easily soluble active substances can also be formulated as an emulsion concentrate by the following method: 20 parts of active substance, 70 parts of xylene, 10 parts of a mixture of a reaction product of an alkylphenol with ethylene oxide and calcium dodecylbenzene-sulphonate are mixed. On dilution with water to the desired concentration, a sprayable emulsion is produced.

EXAMPLE 3

In order to test their action against various storage pests, 2 g of compound No. 1 were mixed with 38 g of talc and the whole was very finely ground. A highly active dusting powder was thus obtained, with which the following results were achieved.

| Test Animals | Minimum Concentration for 100 % Mortality in 24 Hours Exposure Time |
|---|---|
| | mg Active Substance per m² |
| German cockroach (Phyllodromia germanica) | 3 |
| American cockroach (Periplaneta americana) | 3 |
| Russian cockroach (Blatta orientalis) | 25 |
| Blood sucking bug (Rhodnius prolixus) | 25 |
| Domestic cricket (Acheta domestica) | 25 |

EXAMPLE 4

Action against female mosquitoes (*Aedes aegypti*).

10 Female midges are exposed to a coating of the substance to be tested for 6 hours in Petri dishes of 11 cm diameter. In order to manufacture this coating, the bottom of the dish is treated beforehand with 1 ml of acetone solution of compound No. 1 and dried for 1 hour. Solutions containing 1000, 100, 10 and 1 ppm are employed, corresponding to a concentration of 1, 0.1, 0.01 and 0.001 mg/dish respectively. The midges are cooled in ice, and 10 females were counted out into each dish. At each concentration 2 parallel experiments were run on 2 days. All 4 experiments were in agreement with one another, and all resulted in 100% mortality after 45 minutes, at a concentration of 0.001 mg/dish.

EXAMPLE 5

Action against bugs

*Rhodnius prolixus.* As described in Example 6, acetone solutions of the active substance are applied to Petri dishes of 11 cm diameter in such a way as to ensure concentrations of 1 mg, 0.1 mg, 0.01 mg and 0.001 mg per dish (1 mg per dish corresponds to 1 g per 9.4 $m^2$). After the prepared dishes had been dried for 1 hour, 10 bugs in the $L_3$ stage were exposed to the active substance coating for 24 hours. The effect is examined after 45 minutes, 90 minutes, 3 hours, 6 hours and 24 hours.

The experiment was repeated once with a fresh dilution series.

The following mortalities were achieved:

| Compound No. | mg/Dish | After 45 minutes | After 6 hours | After 24 hours |
|---|---|---|---|---|
| 1 | 0.01 | 100 % | 100 % | 100 % |
| 1 | 0.001 | — | 80 % | 100 % |

Similar effects are shown when using compounds No. 3 to 7, 11–15 and 18.

*Cimex lectularius* (bed bug). In a similar test, in which the active substance is used on filter paper in plastic dishes (1 mg per dish corresponds to 1 g per 6 $m^2$), and which was run in 2 repeats with 10 bugs each, active substance No. 1 at a concentration of (a) 1 mg/dish showed 100% mortality after 45 minutes, and (b) at 0.1 mg/dish showed 100% mortality after 6 hours.

EXAMPLE 6

Action against Acarina.

*Rhipicephalus bursa.* 5 Adult hungry ticks are counted into a glass test tube and dipped for 1–2 minutes into 2 ml of an aqueous emulsion containing 100, 10 and 1 ppm of test substance respectively. The test tube is then closed with a standardised cotton-wool pad and turned upside down, so that the active substance emulsion is taken up by the cottonwool. Evaluation takes place after 1 and 2 weeks.

Two repeats are run for each experiment. Compound No. 1 achieved the following values: 100% mortality after 1 week at 100 ppm, 100% mortality after 24 hours at 100 ppm, 100% mortality after 2 weeks at 100 ppm.

EXAMPLE 7

Action against Diptera.

*Lucilia sericata* (larvae). A dilution series is produced using the emulsifiable preparation of active substance No. 1. 2 ml of solution of a certain concentration are mixed with 2 g of chopped horse meat in a 10 ml glass vessel. 20–30 freshly hatched larvae are transferred into these vessels. Evaluation takes place after 24 hours. An active substance concentration of 3 ppm achieved 100% mortality.

Similar results are obtained with compound Nos. 2–10.

EXAMPLE 8

The insecticidal activity of the following compounds was compared

Compound No. 1 (I): phenyl with OCONHCH$_3$ and O–CH(CH$_3$)–CH$_2$–OCH$_3$ substituents Compound (II): phenyl with OCONHCH$_3$ and O–CH$_2$–O–CH(CH$_3$)–CH$_3$ substituents — U. S. Pat. No. 3,492,335, Example 2.

a. Contact action against *Musca domestica:* The test was carried out in a Petri dish applying thereto an acetonic solution of the active ingredient wherein the amount of active ingredient corresponded to 1.5 g/$m^2$ and 0.15 g/$m^2$ respectively. After evaporation of the solvent 20 immobilized polyvalently resistant flies (cooling of the test individuals in a test tube in crused ice) were put on the bottom of the dish whereupon the lid was put on. Within a few minutes the flies were back to normal. The results given below indicate the time after which all the flies were knocked down.

| Compound | amount | time |
|---|---|---|
| I | 1.5 g/$m^2$ | 60 minutes |
|  | 1.15 g/$m^2$ | 5 hours |
| II | 1.5 g/$m^2$ | more than 24 hours |
|  | 1.15 g/$m^2$ | more than 24 hours | b. Contact action against *Blatta germanica:* A 1% dusting agent using as carrier exclusively talcum was prepared by mixing an finely grinding 1 part of active ingredient with 99 parts of talcum. The test was carried out in a Petri dish with 200 mg of active ingredient per $m^2$ which amount was applied by means of a bell-shaped application apparatus and five test animals. The results given below indicate the time after which all test individuals were killed:

| Compound | time |
|---|---|
| I | 5 minutes |
| II | more than 24 hours |

I claim:

1. A pesticidal composition for combatting pests selected from the group consisting of insects and acarids comprising (1) a pesticidally effective amount of the compound of the formula phenyl with O–CO–NHCH$_3$ and O–CH(CH$_3$)–CH$_2$–O–CH$_3$ substituents and (2) a carrier.
2. A method for combatting pests selected from the group consisting of insects and acarids which comprises applying thereto a pesticidally effective amount of the compound of the formula
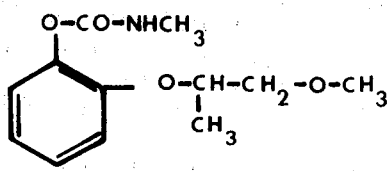
* * * * *